(12) United States Patent
Wang et al.

(10) Patent No.: US 10,070,823 B2
(45) Date of Patent: Sep. 11, 2018

(54) MUTATION SIGNAL PROCESSING METHODS, DEVICES AND MEDICAL DETECTING APPARATUSES

(71) Applicant: SHENZHEN MINDRAY BIO-MEDICAL ELECTRONICS CO., LTD., Shenzhen (CN)

(72) Inventors: Pei Wang, Shenzhen (CN); Shen Luo, Shenzhen (CN); Wenyu Ye, Shenzhen (CN)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 406 days.

(21) Appl. No.: 14/822,585

(22) Filed: Aug. 10, 2015

(65) Prior Publication Data

US 2016/0338650 A1    Nov. 24, 2016

(30) Foreign Application Priority Data

May 22, 2015    (CN) .......................... 2015 1 0267271

(51) Int. Cl.
*A61B 5/00*    (2006.01)

(52) U.S. Cl.
CPC ................................ *A61B 5/7217* (2013.01)

(58) Field of Classification Search
CPC .................................................... A61B 5/7217
See application file for complete search history.

(56) References Cited

U.S. PATENT DOCUMENTS

| 2014/0275878 A1* | 9/2014 | Lisogurski | A61B 5/14551 |
| | | | 600/323 |
| 2015/0190064 A1* | 7/2015 | Kinoshita | A61B 5/024 |
| | | | 600/490 |

\* cited by examiner

*Primary Examiner* — Seahvosh Nikmanesh
(74) *Attorney, Agent, or Firm* — Polsinelli LLP; Kory D. Christensen

(57) ABSTRACT

Mutation signal processing methods, devices and medical detecting apparatuses are described. The method includes detecting whether or not a mutation signal exists in an input signal; if the mutation signal exists in the input signal, processing the input signal by a filter to obtain an output signal, and updating a prestored difference value according to a difference value obtained by subtracting the output signal from the input signal; and if the mutation signal does not exist in the input signal, using a difference value obtained by subtracting the prestored difference value from the input signal as the output signal.

14 Claims, 2 Drawing Sheets

MUTATION SIGNAL PROCESSING METHODS, DEVICES AND MEDICAL DETECTING APPARATUSES

FIELD

The disclosure relates to the field of medical electronics, and more particularly to mutation signal processing methods, devices and medical detecting apparatuses.

BACKGROUND

In a signal processing system, in order to improve the SNR (signal to noise ratio) of a signal, it is necessary to process signals by a high-pass filter or a low-pass filter to remove some interfering signals. Referring to FIG. 1, due to a pacemaker and other reasons, in addition to normal detecting signals (which are not shown in FIG. 1) and interfering signals (which are not shown in FIG. 1), collected original signals may include mutation signals 120. Since the mutation signals 120 could be used to represent the pace-making regularity of the pacemaker, so it is necessary to reserve the mutation signals 120 during signal processing. However, when filtering the interfering signals by the high-pass filter or the low-pass filter, due to the existence of the mutation signals 120, it will inevitably lead to a distortion of the normal detecting signals and the mutation signals 120, thereby affecting the effect of signal processing.

SUMMARY

Embodiments of the present disclosure provide mutation signal processing methods, devices and medical detecting apparatuses, which can be directed to avoid a distortion of an out signal caused by a mutation signal.

According to a first aspect of the present disclosure, a mutation signal processing method is described, including detecting whether or not a mutation signal exists in an input signal; if the mutation signal does not exist in the input signal, processing the input signal by a filter to obtain an output signal, and updating a prestored difference value according to a difference value obtained by subtracting the output signal from the input signal; and if the mutation signal exists in the input signal, using a difference value obtained by subtracting the prestored difference value from the input signal as the output signal.

The step of detecting whether or not a mutation signal exists in an input signal includes determining whether or not the mutation signal exists in the input signal according to amplitude variations of the input signal.

The filter is a filter with time-delay or a filter without time-delay.

If the filter is a filter with time-delay, after detecting whether or not a mutation signal exists in an input signal, the method further includes: if the mutation signal does not exist in the input signal, updating a stored retaining signal according to the input signal, wherein using a difference value obtained by subtracting the prestored difference value from the input signal as the output signal specifically includes processing the stored retaining signal by the filter to obtain a filtered signal; updating the prestored difference value according to a difference value obtained by subtracting the filtered signal from the stored retaining signal; and obtaining the output signal by subtracting the prestored difference value from the input signal after a time-delay.

According to a second aspect of the present disclosure, a mutation signal processing device includes a mutation signal detector, a filter, a first subtractor and a second subtractor, wherein an input end of the mutation signal detector is configured to receive an input signal, a first output end of the mutation signal detector is connected with an input end of the filter, a first input end of the first subtractor is connected with a first output end of the mutation signal detector and the input end of the filter, a second input end of the first subtractor is connected with an output end of the filter, a second output end of the mutation signal detector is connected with a first input end of the second subtractor, and a second input end of the second subtractor is connected with an output end of the first subtractor. The mutation signal detector determines whether or not a mutation signal exists in an input signal, when the mutation signal does not exist in the input signal, and outputs the input signal to the filter and the first subtractor by the first output end of the mutation signal detector. The filter then processes the input signal to obtain an output signal, the first subtractor calculates a difference value obtained by subtracting the output signal from the input signal, and then it uses the difference value to update a prestored difference value. When the mutation signal detector detects that the mutation signal exists in the input signal, the input signal is output to the second subtractor by the second output end of the mutation signal detector, and the second subtractor calculates a difference value obtained by subtracting the prestored difference value from the input signal as the output signal.

The mutation signal detector detects whether or not the mutation signal exists in the input signal according to amplitude variations of the input signal.

The filter is a filter with time-delay or a filter without time-delay.

If the filter is a filter with time-delay, the device further includes a retainer, and a first input end of the retainer is connected with the first output end of the mutation signal detector, a second input end of the retainer is connected with the second output end of the mutation signal detector, and an output end of the retainer is connected with the input end of the filter and the first input end of the first subtractor. The retainer is configured to update a stored retaining signal according to the input signal when the mutation signal does not exist in the input signal, and outputs the stored retaining signal in the retainer to the filter when the mutation signal exists in the input signal.

The device further includes a delayer, wherein an input end of the delayer is connected with the second output end of the mutation signal detector, an output end of the delayer is connected with the first input end of the second subtractor, and the delayer is configured to input the input signal which is output by the mutation signal detector to the second subtractor after a predetermined time-delay.

According to a third aspect of the present disclosure, a medical detecting apparatus includes a mutation signal detector, a filter, a first subtractor and a second subtractor, wherein an input end of the mutation signal detector is configured to receive an input signal, a first output end of the mutation signal detector is connected with an input end of the filter, a first input end of the first subtractor is connected with a first output end of the mutation signal detector and the input end of the filter, a second input end of the first subtractor is connected with the output end of the filter, a second output end of the mutation signal detector is connected with a first input end of the second subtractor, and a second input end of the second subtractor is connected with an output end of the first subtractor. The mutation signal detector determines whether or not a mutation signal exists in an input signal. When the mutation signal does not exist in the input signal, the detector outputs the input signal to the filter and the first subtractor by the first output end of the mutation signal detector. The filter then processes the input signal to obtain an output signal, the first subtractor calculates a difference value obtained by subtracting the output signal from the input signal, and then it uses the difference value to update a prestored difference value. When the mutation signal detector detects that the mutation signal exists in the input signal, the input signal is output to the second subtractor by the second output end of the mutation signal detector, and the second subtractor calculates a difference value obtained by subtracting the prestored difference value from the input signal as the output signal.

Wherein, the mutation signal detector detects whether or not the mutation signal exists in the input signal according to amplitude variations of the input signal.

Wherein, the filter is a filter with time-delay or a filter without time-delay.

If the filter is a filter with time-delay, the medical detecting apparatus further comprises a retainer, and a first input end of the retainer is connected with the first output end of the mutation signal detector, a second input end of the retainer is connected with the second output end of the mutation signal detector, and an output end of the retainer is connected with the input end of the filter and the first input end of the first subtractor. The retainer is then configured to update a stored retaining signal according to the input signal when the mutation signal does not exist in the input signal, and then outputs the stored retaining signal in the retainer to the filter when the mutation signal exists in the input signal.

The medical detecting apparatus further comprises a delayer, wherein an input end of the delayer is connected with the second output end of the mutation signal detector, an output end of the delayer is connected with the first input end of the second subtractor, and the delayer is configured to input the input signal, which is output by the mutation signal detector, to the second subtractor after a predetermined time-delay.

According to the embodiments of the present disclosure, according to the working principle of a high-pass filter, a baseline of the input signal can be removed by the high-pass filter. Therefore, when the mutation signal does not exist in the input signal, the prestored difference value can be obtained by subtracting the output signal from the input signal first, thereby obtaining the baseline of the input signal. When the mutation signal exists in the input signal, the input signal will not pass through the high-pass filter, but subtracts the prestored difference value, which is obtained when the mutation signal does not exist in the input signal to obtain a difference value, and the difference value obtained by subtracting the prestored difference value from the input signal can be taken as the output signal, thereby removing the baseline of the input signal, which avoids distortion of the normal detecting signal and the mutation signal because the mutation signal passes through the high-pass filter. For a low-pass filter, although the baseline of the input signal cannot be removed by the low-pass filter, it will not cause any adverse effects in the present disclosure.

BRIEF DESCRIPTION OF THE DRAWINGS

In order to illustrate the embodiments or existing technical solutions more clearly, a brief description of drawings that assists the description of embodiments of the invention or existing art will be provided below. It would be apparent that the drawings in the following description are only for some of the embodiments of the invention. A person having ordinary skills in the art will be able to obtain other drawings on the basis of these drawings without paying for any creative work.

DETAILED DESCRIPTION OF ILLUSTRATED EMBODIMENTS

The following text, in conjunction with the accompanying drawings according to various embodiments, clearly describes technical proposals according to various embodiments. It would be obvious that the described embodiments are part but not all of the embodiments. All other embodiments obtained by persons having ordinary skills without paying for any creative work based on the illustrated embodiments should all be within the scope according to various embodiments.

Figure 2:
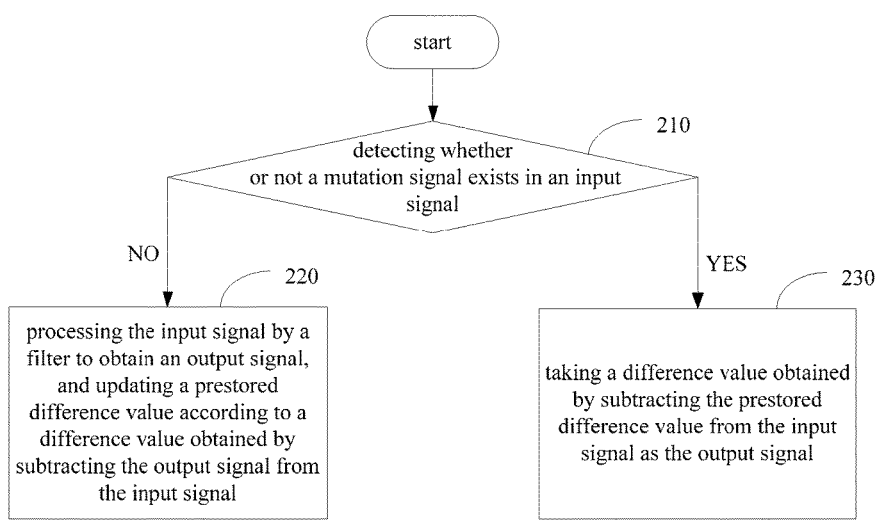
FIG. 2 is a flowchart of a mutation signal processing method according to one embodiment of the present disclosure.

FIG. 2 is a flowchart of a mutation signal processing method according to one embodiment of the present disclosure. The mutation signal processing method according to the present embodiment includes the following steps:

Step 210: detecting whether or not a mutation signal exists in an input signal.

Specifically, the mutation signal detector determines whether or not the mutation signal exists in the input signal according to amplitude variations of the input signal. For example, the mutation signal detector determines whether or not the mutation signal exists in the input signal in accordance with whether or not the amplitude of the input signal exceeds a threshold value in an instant or within a period of time. If the mutation signal does not exist in the input signal, the method enters step 220. If the mutation signal exists in the input signal, the method enters step 230.

The threshold value is associated with the amplitude of the input signal. In general, the greater the amplitude of the input signal is, the greater the threshold value is set, and the smaller the amplitude of the input signal is, the smaller the threshold value is set, which will not be restricted here in embodiments of the present disclosure.

It should be understood that, in other embodiments, the mutation signal detector determines whether or not the mutation signal exists in the input signal by some other means. For example, the mutation signal detector determines whether or not the mutation signal exists in the input signal according to variations of the input signal energy.

Step 220: processing the input signal by a filter to obtain an output signal, and updating a prestored difference value according to a difference value obtained by subtracting the output signal from the input signal.

Specifically, in a first mode, the filter is a filter without time-delay, that is, after the input signal is processed by the filter, an output signal can be obtained immediately. If the mutation signal does not exist in the input signal, the output signal can be obtained after the input signal is processed by the filter, and the difference value obtained by subtracting the output signal from the input signal can be used to update the prestored difference value.

In a second mode, the filter is a filter with time-delay, that is, after the input signal is input to the filter, a corresponding output signal will be obtained in the output end of the filter after a predetermined time-delay. If the mutation signal exists in the input signal, the output signal can be obtained after the input signal is processed by the filter, and the difference value obtained by subtracting the output signal from the input signal can be used to update the prestored difference value. Specifically, the input signal can be used to update a stored retaining signal, then the output signal can be obtained after the stored retaining signal is processed by the filter, and then a difference value obtained by subtracting the output signal from the stored retaining signal can be used to update the prestored difference value.

Step 230: taking a difference value obtained by subtracting the prestored difference value from the input signal as the output signal.

Specifically, in the first mode, the filter is a filter without time-delay. The output signal can be obtained by subtracting the prestored difference value from the input signal, where the prestored difference value is a difference value that is calculated when the mutation signal does not exist in the input signal. The prestored difference value is an amplitude of a baseline, which is calculated when the mutation signal does not exist in the input signal, while the amplitude of the baseline is constant. Therefore, when the mutation signal exists in the input signal, by subtracting the prestored difference value from the input signal to obtain the output signal, the amplitude of the baseline can remain consistent.

In the second mode, the filter is a filter with time-delay. Similar to the first mode, the output signal can be obtained by subtracting the prestored difference value from the input signal.

Figure 3:
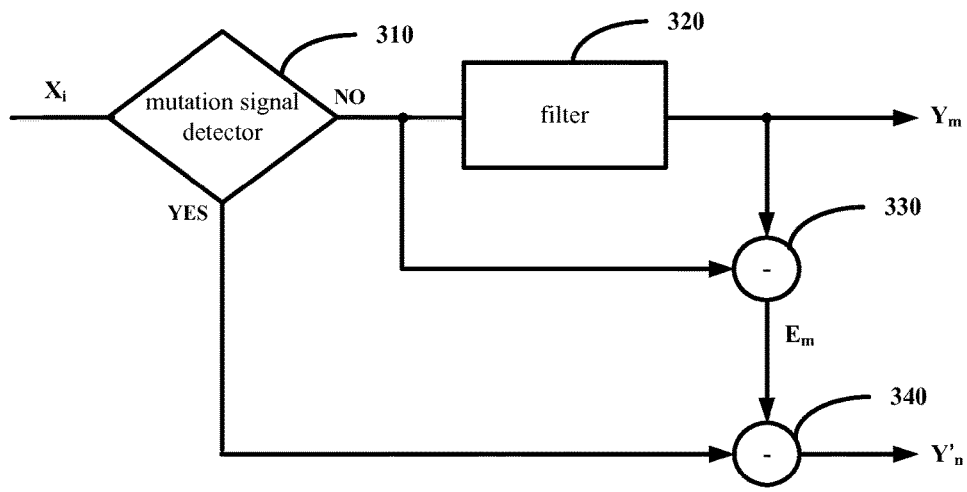
FIG. 3 is a structure diagram of a mutation signal processing device according to one embodiment of the present disclosure.

FIG. 3 is a structure diagram of a mutation signal processing device according to one embodiment of the present disclosure, and will be described in detail as follows. In a first mode, within a filter system, there is a filter without time-delay, and a mutation signal processing device in one embodiment includes a mutation signal detector 310, a filter 320, a first subtractor 330 and a second subtractor 340. An input end of the mutation signal detector 310 is configured to receive an input signal; a first output end of the mutation signal detector 310 is connected with an input end of the filter 320. A first input end of the first subtractor 330 is connected to a common end of the mutation signal detector 310 and the filter 320, a second input end of the first subtractor 330 is connected with an output end of the filter 320, a first input end of the second subtractor 340 is connected with a second output end of the mutation signal detector 310, and a second input end of the second subtractor 340 is connected with an output end of the first subtractor 330.

The mutation signal does not exist in the input signal at the time $T_1$ and the time $T_2$, and the mutation signal exists in the input signal at the time $T_3$ and the time $T_4$.

At the time $T_1$, an input signal $X_1$ is input to the mutation signal detector 310, and the mutation signal detector 310 determines whether or not the mutation signal exists in the input signal $X_1$ at the time $T_1$ in accordance with whether or not an amplitude of the input signal $X_1$ exceeds a threshold value. If the mutation signal does not exist in the input signal, the input signal $X_1$ will be input to the filter 320 to filter out the interfering signal which contains a baseline signal in the input signal $X_1$, thereby obtaining an output signal $Y_1$ at the time $T_1$. Simultaneously, the input signal $X_1$ and the output signal $Y_1$ at the time $T_1$ are input to the first subtractor 330 to obtain a prestored difference value $E_1$ by subtracting the output signal $Y_1$ at the time $T_1$ from the input signal $X_1$ at the time $T_1$. That is, the prestored difference value $E_1$ is the interfering signal filtered by the filter 320 at the time $T_1$.

At the time $T_2$, an input signal $X_2$ is input to the mutation signal detector 310, which determines whether or not the mutation signal exists in the input signal $X_2$ at the time $T_2$ in accordance with whether or not an amplitude of the input signal $X_2$ exceeds the threshold value. If the mutation signal does not exist in the input signal, the input signal $X_2$ will be input to the filter 320 to filter out the interfering signal, which contains a baseline signal in the input signal $X_2$, thereby obtaining an output signal $Y_2$ at the time $T_2$. Simultaneously, the input signal $X_2$ the output signal $Y_2$ at the time $T_2$ are input to the first subtractor 330 to obtain a prestored difference value $E_2$ by subtracting the output signal $Y_2$ at the time $T_2$ from the input signal $X_2$ at the time $T_2$. That is, the prestored difference value $E_2$ is the interfering signal filtered by the filter 320 at the time $T_2$.

At the time $T_3$, an input signal $X_3$ is input to the mutation signal detector 310, which determines whether or not the mutation signal exists in the input signal $X_3$ at the time $T_3$ in accordance with whether or not an amplitude of the input signal $X_3$ exceeds the threshold value. If the mutation signal exists in the input signal, the input signal $X_3$, which contains a mutation signal, will not be input to the filter 320, but will be directly output to the second subtractor 340. Simultaneously, the prestored difference value $E_2$ will be output to the second subtractor 340 by the first subtractor 330, and then an output signal $Y'_3$ can be obtained by subtracting the prestored difference value $E_2$ from the input signal $X_3$ at the time $T_3$. Since the input signal $X_3$ will not be input to the filter 320 and the first subtractor 330, the output of the first subtractor 330 remains to be the prestored difference value $E_2$.

At the time $T_4$, an input signal $X_4$ is input to the mutation signal detector 310, which determines whether or not the mutation signal exists in the input signal $X_4$ at the time $T_4$ in accordance that whether or not an amplitude of the input signal $X_4$ exceeds the threshold value. If the mutation signal exists in the input signal, the input signal $X_4$, which contains a mutation signal, will not be input to the filter 320, but will be directly output to the second subtractor 340. Simultaneously, the prestored difference value $E_2$ will be output to the second subtractor 340 by the first subtractor 330, and then an output signal $Y'_4$ can be obtained by subtracting the prestored difference value $E_2$ from the input signal $X_4$ at the time $T_4$.

Therefore, when the mutation signal exists in the input signal, the input signal will not be input to the filter for filtering, but it subtracts the interfering signal, which is obtained when the mutation signal does not exist in the input signal, thereby avoiding a distortion caused by the filter.

Figure 4:
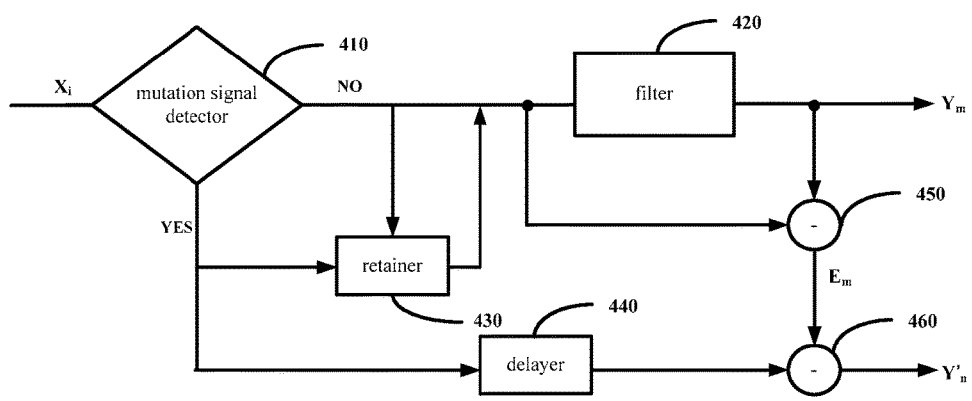
FIG. 4 is a structure diagram of a mutation signal processing device according to another embodiment of the present disclosure.

FIG. 4 is a structure diagram of a mutation signal processing device according to another embodiment of the present disclosure, and will be described as follows. In a second mode, the filter is a filter with time-delay. The mutation signal processing device in another embodiment includes a mutation signal detector 410, a filter 420, a retainer 430, a delayer 440, a first subtractor 450 and a second subtractor 460. An input end of the mutation signal detector 410 is configured to receive an input signal, a first output end of the mutation signal detector 410 is connected with an input end of the filter 420, a first input end of the retainer 430 is connected with a first output end of the mutation signal detector 410, a second input end of the retainer 430 is connected with a second output end of the mutation signal detector 410, an output end of the retainer 430 is connected with the first output end of the mutation signal detector 410, an input end of the delayer 440 is connected with the second output end of the mutation signal detector 410, an output end of the delayer 440 is connected with a first input end of the second subtractor 460, a first input end of the first subtractor 450 is connected to a common end of the mutation signal detector 410 and the filter 420, a second input end of the first subtractor 450 is connected with the output end of the filter 420, and a second input end of the second subtractor 460 is connected with an output end of the first subtractor 450.

The mutation signal does not exist in the input signal at the time $T_1$ and the time $T_2$, and the mutation signal exists in the input signal at the time $T_3$ and the time $T_4$.

At the time $T_1$, an input signal $X_1$ is input to the mutation signal detector 410, and the mutation signal detector 410 determines whether or not the mutation signal exists in the input signal $X_1$ at the time $T_1$ in accordance with whether or not the amplitude of the input signal $X_1$ exceeds a threshold value. If the mutation signal does not exist in the input signal, the input signal $X_1$ will be input to the filter 420 for filtering, and simultaneously, the input signal $X_1$ will be input to the retainer 430 for retaining. Since the filter is a filter with time-delay, after a predetermined time-delay (assuming that the predetermined time-delay is five times), the filter 420 can output an output signal $Y_1$ at the time $T_6$, where the interfering signal which contains a baseline signal in the input signal $X_1$ has been filtered out.

At the time $T_2$, an input signal $X_2$ is input to the mutation signal detector 410, and the mutation signal detector 410 determines whether or not the mutation signal exists in the input signal $X_2$ at the time $T_2$ in accordance with whether or not the amplitude of the input signal $X_2$ exceeds the threshold value. If the mutation signal does not exist in the input signal, the input signal $X_2$ will be input to the filter 420 for filtering, and simultaneously, the input signal $X_2$ will be input to the retainer 430 for retaining. Since the filter is a filter with time-delay, after a predetermined time delay (assuming that the predetermined time delay is five times), the filter 420 can output an output signal $Y_2$ at the time $T_7$.

At the time $T_3$, an input signal $X_3$ is input to the mutation signal detector 410, and the mutation signal detector 410 determines whether or not the mutation signal exists in the input signal $X_3$ at the time $T_3$ in accordance with whether or not the amplitude of the input signal $X_3$ exceeds the threshold value. If the mutation signal exists in the input signal, the input signal $X_2$ is input to the retainer 430 for retaining at the time $T_2$ will be output to the filter 420. Simultaneously, the input signal $X_3$, which contains the mutation signal, is input to the delayer 440. The time-delay of the delayer 440 is the same as the predetermined time-delay; therefore, the input signal $X_3$, which contains the mutation signal, will be output to the second subtractor 460 at the time $T_8$. Simultaneously, the input signal $X_2$ is output to the first subtractor 450 by the retainer 430, and then a prestored difference value $E_2$ can be obtained by subtracting the output signal $Y_2$ input to the first subtractor 450 from the input signal $X_2$. In the second subtractor 460, an output signal $Y_8$ at the time $T_8$ can be obtained by subtracting the prestored difference value $E_2$ from the input signal $X_3$.

At the time $T_4$, an input signal $X_4$ is input to the mutation signal detector 410, and the mutation signal detector 310 determines whether or not the mutation signal exists in the input signal $X_4$ at the time $T_4$ in accordance with whether or not amplitude of the input signal $X_4$ exceeds the threshold value. If the mutation signal exists in the input signal, the input signal $X_2$ is input to the retainer 430 for retaining at the time $T_2$ it will be output to the filter 420. Simultaneously, the input signal $X_4$, which contains the mutation signal, is input to the delayer 440. The time-delay of the delayer 440 is the same as the predetermined time-delay; therefore, the input signal $X_4$, which contains the mutation signal, will be output to the second subtractor 460 at the time $T_9$. Simultaneously, the input signal $X_2$ is output to the first subtractor 450 by the retainer 430, and then the prestored difference value $E_2$ can be obtained by subtracting the output signal $Y_2$ input to the first subtractor 450 from the input signal $X_2$. In the second subtractor 460, an output signal $Y_9$ at the time $T_9$ can be obtained by subtracting the prestored difference value $E_2$ from the input signal $X_4$.

Therefore, when the mutation signal exists in the input signal, the input signal will not be input to the filter for filtering, but it subtracts the interfering signal, which is obtained when the mutation signal does not exist in the input signal, thereby avoiding a distortion caused by the filter.

According to the embodiments of the present disclosure described above, and according to the working principle of a high-pass filter, the baseline of the input signal can be removed by the high-pass filter. Therefore, when the mutation signal does not exist in the input signal, the prestored difference value can be obtained by subtracting the output signal from the input signal first, thereby obtaining the baseline of the input signal. When the mutation signal exists in the input signal, the input signal will not pass through the high-pass filter, but it subtracts the prestored difference value, which is obtained when the mutation signal does not exist in the input signal, to obtain a difference value, and the difference value obtained by subtracting the prestored difference value from the input signal can be used as the output signal, thereby removing the baseline of the input signal, which avoids distortion of the normal detecting signal and the mutation signal because the mutation signal passes through the high-pass filter. For a low-pass filter, although the baseline of the input signal cannot be removed by the low-pass filter, it will not cause any adverse effects in the present disclosure.

Figure 1:
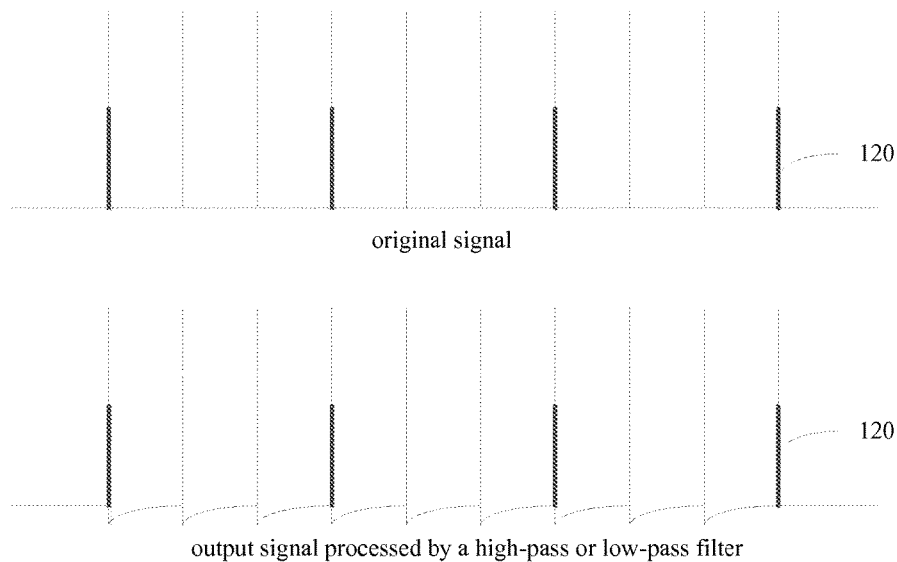
FIG. 1 is a comparison chart of output signals processed by a high-pass or low-pass filter and original signals according to a prior art.

As described above, an undistorted signal can be obtained as shown in FIG. 1 according to the present disclosure, which brings a good experimental result.

A medical detecting apparatus is further provided in one embodiment of the present disclosure, wherein the medical detecting apparatus includes the mutation signal processing device as described above. For example see FIGS. 3 and 4, and other related descriptions herein.

A person having ordinary skills in the art can understand that part or all of the processes in the methods described above may be implemented by a computer program instructing hardware. The program may be stored in a computer readable storage medium. When executed, the program may execute processes in the above-mentioned embodiments. The storage medium may be a magnetic disk, an optical disk, a Read-Only Memory (ROM), a Random Access Memory (RAM), etc.

The foregoing descriptions are merely embodiments of the present disclosure and are not intended to limit the scope of the present disclosure. Any variation or replacement made by persons of ordinary skills in the art without departing from the spirit of the present disclosure shall fall within the scope of the present disclosure. Therefore, the scope of the present disclosure shall be subject to the appended claims.

What is claimed is:

1. A mutation signal processing method, comprising:
processing an input signal using a mutational signal detector to determine whether or not a mutation signal exists in the input signal;
if the mutation signal does not exist in the input signal;
processing the input signal by a filter to obtain an output signal;
using a subtractor to calculate a first difference value by subtracting the output signal from the input signal; and
updating a prestored difference value according to the first difference value;
if the mutation signal exists in the input signal:
using a subtractor to calculate a second difference value by subtracting the prestored difference value from the input signal; and
outputting the second difference value as the output signal.

2. The method according to claim 1, wherein the step of detecting whether or not a mutation signal exists in an input signal comprises:
determining whether or not the mutation signal exists in the input signal according to amplitude variations of the input signal.

3. The method according to claim 1, wherein the filter is a filter with time-delay or a filter without time-delay.

4. The method according to claim 3, wherein the filter is a filter with time-delay, after the step of detecting whether or not a mutation signal exists in an input signal, the method further comprising:
if the mutation signal does not exist in the input signal, updating a stored retaining signal according to the input signal;
wherein the step of using a difference value, obtained by subtracting the prestored difference value from the input signal, as the output signal, specifically comprising:
processing the stored retaining signal by the filter to obtain a filtered signal;
updating the prestored difference value according to a difference value obtained by subtracting the filtered signal from the stored retaining signal; and
obtaining the output signal by subtracting the prestored difference value from the input signal after a time-delay.

5. A mutation signal processing device, comprising:
a mutation signal detector;
a filter;
a first subtractor; and
a second subtractor, wherein an input end of the mutation signal detector is configured to receive an input signal, a first output end of the mutation signal detector is connected with an input end of the filter, a first input end of the first subtractor is connected with a first output end of the mutation signal detector and the input end of the filter, a second input end of the first subtractor is connected with an output end of the filter, a second output end of the mutation signal detector is connected with a first input end of the second subtractor, and a second input end of the second subtractor is connected with an output end of the first subtractor;
the mutation signal detector determines whether or not a mutation signal exists in an input signal, when the mutation signal does not exist in the input signal, and outputs the input signal to the filter and the first subtractor by the first output end of the mutation signal detector, the filter processes the input signal to obtain an output signal, and the first subtractor calculates a difference value obtained by subtracting the output signal from the input signal and uses the difference value to update a prestored difference value; when the mutation signal detector detects that the mutation signal exists in the input signal, the input signal is output to the second subtractor by the second output end of the mutation signal detector, and the second subtractor calculates a difference value obtained by subtracting the prestored difference value from the input signal as the output signal.

6. The device according to claim 5, wherein the mutation signal detector detects whether or not the mutation signal exists in the input signal according to amplitude variations of the input signal.

7. The device according to claim 5, wherein the filter is a filter with time-delay or a filter without time-delay.

8. The device according to claim 7, wherein the filter is a filter with time-delay, the device further comprising a retainer, and a first input end of the retainer is connected with the first output end of the mutation signal detector, a second input end of the retainer is connected with the second output end of the mutation signal detector, and an output end of the retainer is connected with the input end of the filter and the first input end of the first subtractor;
the retainer is configured to update a stored retaining signal according to the input signal when the mutation signal does not exist in the input signal, and outputs the stored retaining signal in the retainer to the filter when the mutation signal exists in the input signal.

9. The device according to claim 8, the device further comprising a delayer, wherein an input end of the delayer is connected with the second output end of the mutation signal detector, an output end of the delayer is connected with the first input end of the second subtractor, and the delayer is configured to input the input signal which is output by the mutation signal detector to the second subtractor after a predetermined time-delay.

10. A medical detecting apparatus, comprising: a mutation signal detector, a filter, a first subtractor, and a second subtractor, wherein an input end of the mutation signal detector is configured to receive an input signal, a first output end of the mutation signal detector is connected with an input end of the filter, a first input end of the first subtractor is connected with a first output end of the mutation signal detector and the input end of the filter, a second input end of the first subtractor is connected with an output end of the filter, a second output end of the mutation signal detector is connected with a first input end of the second subtractor, and a second input end of the second subtractor is connected with an output end of the first subtractor;
the mutation signal detector determines whether or not a mutation signal exists in an input signal, and when the mutation signal does not exist in the input signal, it outputs the input signal to the filter and the first subtractor by the first output end of the mutation signal detector, the filter processes the input signal to obtain an output signal, and the first subtractor calculates a difference value obtained by subtracting the output signal from the input signal and uses the difference value to update a prestored difference value; when the mutation signal detector detects that the mutation signal exists in the input signal, the input signal is output to the second subtractor by the second output end of the mutation signal detector, and the second subtractor calculates a difference value obtained by subtracting the prestored difference value from the input signal as the output signal.

11. The medical detecting apparatus according to claim 10, wherein the mutation signal detector detects whether or not the mutation signal exists in the input signal according to amplitude variations of the input signal.

12. The medical detecting apparatus according to claim 10, wherein the filter is a filter with time-delay or a filter without time-delay.

13. The medical detecting apparatus according to claim 12, wherein the filter is a filter with time-delay, the device further comprising a retainer, and a first input end of the retainer is connected with the first output end of the mutation signal detector, a second input end of the retainer is connected with the second output end of the mutation signal detector, and an output end of the retainer is connected with the input end of the filter and the first input end of the first subtractor;

the retainer is configured to update a stored retaining signal according to the input signal when the mutation signal does not exist in the input signal, and outputs the stored retaining signal in the retainer to the filter when the mutation signal exists in the input signal.

14. The medical detecting apparatus according to claim 13, the medical detecting apparatus further comprising a delayer, wherein an input end of the delayer is connected with the second output end of the mutation signal detector, an output end of the delayer is connected with the first input end of the second subtractor, and the delayer is configured to input the input signal which is output by the mutation signal detector to the second subtractor after a predetermined time-delay.

* * * * *